US012661249B2

(12) United States Patent
McGuinn et al.

(10) Patent No.: US 12,661,249 B2
(45) Date of Patent: Jun. 23, 2026

(54) SYSTEMS FOR DRY TISSUE VALVES AND METHODS OF USE THEREOF

(71) Applicant: Medtronic, Inc., Minneapolis, MN (US)

(72) Inventors: Alan T. McGuinn, Oranmore (IE); Conleth A. Mullen, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/914,513

(22) Filed: Oct. 14, 2024

(65) Prior Publication Data

US 2025/0134685 A1 May 1, 2025

Related U.S. Application Data

(60) Provisional application No. 63/593,782, filed on Oct. 27, 2023.

(51) Int. Cl.
*A61F 2/95* (2013.01)
*A61F 2/00* (2006.01)
*A61F 2/24* (2006.01)

(52) U.S. Cl.
CPC .......... *A61F 2/9524* (2020.05); *A61F 2/0095* (2013.01); *A61F 2/2427* (2013.01); *Y10T 29/49913* (2015.01); *Y10T 29/49929* (2015.01)

(58) Field of Classification Search
CPC .. A61F 2/0095; A61F 2/9524; Y10T 29/4991; Y10T 29/4992
See application file for complete search history.

(56) References Cited

U.S. PATENT DOCUMENTS

| | | | |
|---|---|---|---|
| 7,415,861 B2 * | 8/2008 | Sokel | A61F 2/9524 72/402 |
| 7,487,579 B2 | 2/2009 | Eidenschink et al. | |
| 8,312,614 B2 | 11/2012 | Sokel | |
| 9,051,065 B2 | 6/2015 | Pacetti | |
| 9,114,010 B2 | 8/2015 | Gaschino et al. | |
| 10,709,591 B2 | 7/2020 | Fox et al. | |
| 2013/0152659 A1 | 6/2013 | Maimon et al. | |
| 2013/0238088 A1 * | 9/2013 | Navia | A61F 2/2418 623/2.11 |
| 2014/0260097 A1 * | 9/2014 | Avery | A61F 2/9524 72/367.1 |
| 2020/0352760 A1 | 11/2020 | Karalnik et al. | |
| 2021/0030533 A1 | 2/2021 | Tamir et al. | |

OTHER PUBLICATIONS

Extended European Search Report, EP Application No. 24207516.6, mailed Mar. 26, 2025, 9 pages.

* cited by examiner

*Primary Examiner* — Jermie E Cozart
(74) *Attorney, Agent, or Firm* — Medler Ferro Woodhouse Mills PLLC

(57) ABSTRACT

A dry valve crimping and loading system includes packaging, a crimper disposed in the packaging, and a dry valve prosthesis disposed within a crimper chamber of the crimper. The crimper chamber has a first volume in an expanded state a second volume in a collapsed state, wherein the first volume is greater than the second volume. The crimper is configured to transition the dry valve prosthesis from an uncompressed state to a compressed state when the crimper chamber transitions from the expanded state to the collapsed state to expel the glycerol from the dry valve prosthesis as the crimper transitions the dry valve prosthesis from the uncompressed state to the compressed state.

2 Claims, 15 Drawing Sheets

1

SYSTEMS FOR DRY TISSUE VALVES AND METHODS OF USE THEREOF

CROSS-REFERENCE TO RELATED APPLICATIONS

This application claims the benefit of U.S. Provisional Patent Application Ser. No. 63/593,782, filed Oct. 27, 2023, the entire content of which is incorporated herein by reference.

FIELD

The present disclosure is related to systems and methods for crimping a dry prosthetic valve and loading the crimped dry prosthetic valve into a delivery system.

BACKGROUND

Patients suffering from various medical conditions or diseases may require surgery to install a valve prosthesis. For example, valve regurgitation or stenotic calcification of leaflets of a heart valve may be treated with a heart valve replacement procedure. A traditional surgical valve replacement procedure requires a sternotomy and a cardiopulmonary bypass, which creates significant patient trauma and discomfort. Traditional surgical valve procedures may also require extensive recuperation times and may result in life-threatening complications.

One alternative to a traditional surgical valve replacement procedure is delivering valve prosthesis using minimally invasive techniques. For example, a prosthetic valve can be percutaneously and transluminally delivered and deployed at the site of the diseased heart valve through catheter-based delivery systems. Such a valve prosthesis can be delivered while in a low-profile or compressed configuration so that the valve prosthesis can be advanced through the patient's vasculature. Once positioned at the treatment site, the valve prosthesis can be expanded to engage tissue at the diseased heart valve region to, for instance, hold the valve prosthesis in position.

Known valve prostheses include a stent frame supporting a valve structure. The valve structure can assume a variety of forms, and can be formed, for example, from tissue made from one or more biocompatible synthetic materials, synthetic polymers, autograft tissue, homograft tissue, xenograft tissue, or one or more other suitable materials. In some embodiments, the valve structure can be formed, for example, from bovine, porcine, equine, ovine and/or other suitable animal tissues. The valve structure can be formed from heart valve tissue, pericardium, and/or other suitable tissue. In some embodiments, the valve structure can include or form one or more leaflets. For example, the valve structure can be in the form of a tri-leaflet bovine pericardium valve, a bi-leaflet valve, or another suitable valve.

Valve prostheses using animal tissues are often packaged in containers filled with solution, such as glutaraldehyde, for sterilizing and preserving the valve prosthesis prior to attachment to a delivery device for delivery to a patient. However, glutaraldehyde is considered potentially toxic and creates potential calcium binding sites within the tissue that can lead to calcification in vivo. Accordingly, "dry" tissue valves have also been developed. In "dry" tissue valves, the bioprosthetic tissue is dehydrated in a glycerol/ethanol mixture, sterilized with ethylene oxide, and the final product is packaged "dry". This process circumvents the potential toxicity and calcification effects of glutaraldehyde as a sterilant and storage solution. However, glycerol is tacky and may pose handling challenges. Glycerol coated tissue may also be prone to particulate. Further, the glycerol molecule is large which may result in more force/time to compress tissue (expelling glycerol molecule from tissue). Further, the fully crimped dry tissue can take a permanent set (crease) with time. Still further, the tacky nature of glycerol may result in high drag (e.g., during insertion of the valve prosthesis into a capsule of a delivery system).

Accordingly, the present application is directed to systems for use with dry tissue valves such that the advantages of dry tissue valves (e.g., no gluteralehyde) are realized while the disadvantages of glycerol are minimized.

BRIEF SUMMARY

In an example of the present disclosure, a dry valve crimping and loading system includes packaging, a crimper disposed in the packaging, and a dry valve prosthesis disposed within the crimper. The crimper includes a crimper chamber having an expanded state and a collapsed state. The dry valve prosthesis is disposed within the crimper chamber of the crimper with the crimper chamber in the expanded state and the dry valve prosthesis in an uncompressed state. The dry valve prosthesis includes a frame and a dry prosthetic valve coupled to the valve, the dry prosthetic valve including glycerol. The crimper chamber has a first volume in the expanded state a second volume in the collapsed state, wherein the first volume is greater than the second volume. The crimper is configured to transition the dry valve prosthesis from the uncompressed state to a compressed state when the crimper chamber transitions from the expanded state to the collapsed state. The crimper is configured to expel the glycerol from the dry prosthetic valve as the crimper transitions the dry prosthetic valve from the uncompressed state to the compressed state.

In another example hereof, in the dry valve crimping and loading system of any of the preceding or following examples, the crimper includes a handle configured to transition the crimper from the expanded state to the collapsed state.

In another example hereof, in the dry valve crimping and loading system of any of the preceding or following examples, the crimper includes a ratcheting mechanism configured to transition the crimper from the expanded state to the collapsed state.

In another example hereof, in the dry valve crimping and loading system of any of the preceding or following examples, the crimper includes a force limiter configured to limit the amount of force exerted on the dry valve prosthesis by the crimper.

In another example hereof, in the dry valve crimping and loading system of any of the preceding or following examples, the crimper further includes a force sensor and an indicator configured to indicate when sufficient force from the crimper is exerted onto the dry valve prosthesis.

In another example hereof, in the dry valve crimping and loading system of any of the preceding or following examples, the indicator is visual, auditory, kinesthetic, haptic, and/or combinations thereof.

In another example hereof, in the dry valve crimping and loading system of any of the preceding or following examples, the crimper includes a plurality of crimper elements, the distal ends of the plurality of crimper elements defining the crimper chamber, wherein the crimper includes a plurality of pistons, the pistons coupled to a corresponding one of the plurality of crimper elements, and wherein the pistons are configured to push the distal ends of the crimper elements towards a center of the crimper to transition the crimper chamber from the expanded state to the collapsed state.

In another example hereof, in the dry valve crimping and loading system of any of the preceding or following examples, the pistons are driven hydraulically, pneumatically, and/or electronically.

In another example hereof, a method for crimping and loading a dry valve prosthesis onto a delivery system comprises: removing a dry valve crimping and loading system from packaging, the dry valve crimping and loading system including a crimper and the dry valve prosthesis disposed within a crimping chamber of the crimper, the dry valve prosthesis including a frame and a dry prosthetic valve coupled to the frame; actuating the crimper to transition the crimper chamber from an expanded state to a collapsed state and to transition the dry valve prosthesis from an uncompressed state to a compressed state.

In another example hereof, the method of any of the preceding or following examples further comprises loading the dry valve prosthesis onto a catheter.

In another example hereof, in the method of any of the preceding or following examples, loading the dry valve prosthesis onto the catheter comprises insert a distal end of the catheter into the crimper chamber such that actuating the crimper to transition the dry valve prosthesis to the compressed state also loads the dry valve prosthesis onto the catheter.

In another example hereof, in the method of any of the preceding or following examples, the crimper includes a handle, wherein actuation of the handle transitions the crimper from the expanded state to the collapsed state and the dry valve prosthesis from the uncompressed state to the compressed state.

In another example hereof, in the method of any of the preceding or following examples, actuating the crimper to transition the dry valve prosthesis from the uncompressed state to the compressed state expels glycerol from the dry valve prosthesis.

In another example hereof, the method of any of the preceding or following examples further comprises placing the crimper with the dry valve prosthesis disposed in the crimper chamber into a rinse tray after removing the crimper dry valve crimping and loading system from the packaging and before actuating the crimper.

In another example hereof, in the method of any of the preceding or following examples, the rinse tray is at least partially filled with a rinse fluid configured to expel glycerol from the dry valve prosthesis.

In another example hereof, a method for crimping and loading a dry valve prosthesis onto a delivery system comprises: at least partially filling a rinse tray with a rinse solution; actuating the crimper to transition the crimper from an expanded state to a collapsed state and to transition the dry valve prosthesis from an uncompressed state to a compressed state; releasing or disengaging the crimper to transition the crimper form the collapsed state to the expanded state and to transition the dry valve prosthesis from the compressed state to the uncompressed state; removing the crimper and the dry valve prosthesis from the rinse tray; disposing a distal end of a delivery system within the dry valve prosthesis; actuating the crimper to transition the crimper from the expanded state to the collapsed state and to transition the dry valve prosthesis from an uncompressed state to a compressed state onto the distal end of the delivery system; coupling the dry valve prosthesis to the delivery system; removing the crimper from the dry valve prosthesis and the delivery system; and sterilizing the delivery system and the dry valve prosthesis.

In another example hereof, in the method of any of the preceding or following examples, the crimper of the dry valve crimping and loading system includes a handle, wherein actuation of the handle transitions the crimper from the expanded state to the collapsed state and the dry valve prosthesis from the uncompressed state to the compressed state.

In another example hereof, in the method of any of the preceding or following examples, actuating the crimper to transition the crimper from the expanded state to the collapsed state and to transition the dry valve prosthesis from the uncompressed state to the compressed state expels glycerol from the dry valve prosthesis.

In another example hereof, in the method of any of the preceding or following examples, actuating the crimper and releasing or disengaging the crimper is repeated one or more times.

In another example hereof, in the method of any of the preceding or following examples, the rinse solution is exchanged at least one time during following actuating and releasing or disengaging the crimper.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings may not be to scale.

DETAILED DESCRIPTION

Figure 1:
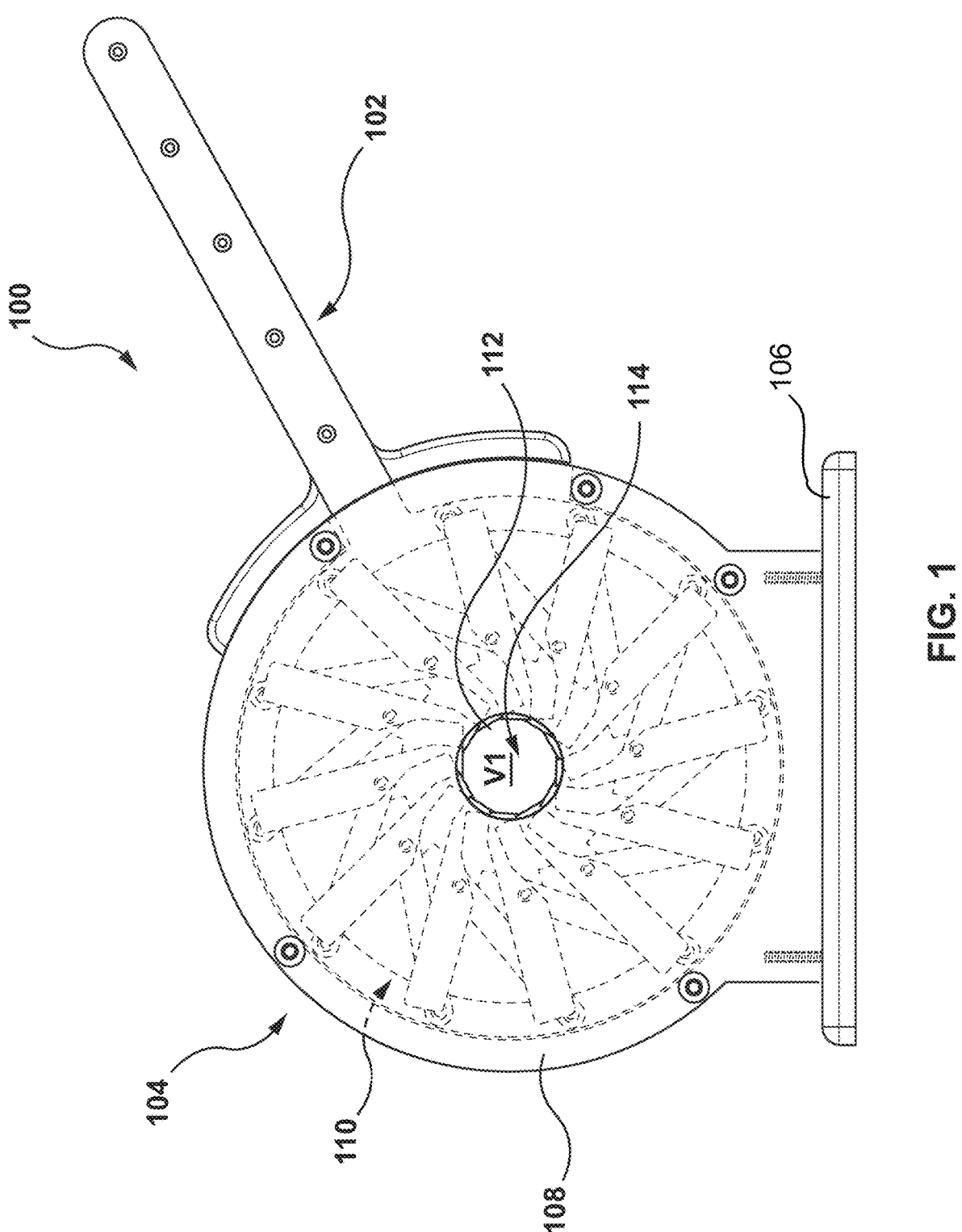
FIG. 1 depicts a side view of a crimper according to embodiments hereof.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a delivery system. The following detailed description is merely exemplary in nature and is not intended to limit the disclosure. Furthermore, there is no intention to be bound by any expressed or implied theory presented in the preceding field of the invention, background, summary, or the following detailed description.

As used in this specification, the singular forms "a," "an" and "the" specifically also encompass the plural forms of the terms to which they refer, unless the content clearly dictates otherwise. Further, numerical terms such as "first," "second," "third," etc. used herein are not meant to be limiting such that use of the term "second" when referring to a part in the specification does not mean that there necessarily is a "first" part in order to fall within the scope of the disclosure. Instead, such numbers are merely describing that the particular embodiment being described has a "first" part and a "second" part. The disclosure is instead defined by the claims, in which one or more of the numbered parts may be claimed.

The terms "distal" and "proximal" when used in the following description to refer to a delivery system or catheter are with respect to a position or direction relative to the treating clinician or the handle of the delivery system/ catheter. Thus, "distal" and "distally" refer to positions distant from, or in a direction away from the treating clinician or handle, and the terms "proximal" and "proximally" refer to positions near, or in a direction toward the clinician or handle.

The term "dry" when used in the following description to refer to tissue of prosthetic valves of heart valve prostheses refers to tissue that has been treated with glycerine, alcohols, and/or combinations thereof resulting in tissue in a "dry" state rather than a wet state with excess glutaraldehyde. Further, such "dry" prosthetic valves do not need to be stored in liquid, such as glutaraldehyde.

Embodiments hereof relate to dry valve crimping and loading systems and methods of crimping and loading a dry valve prosthesis onto a delivery system. In embodiments hereof, as will be described in more detail herein, the dry valve crimping and loading system includes a crimper and a dry valve prosthesis.

Figure 2:
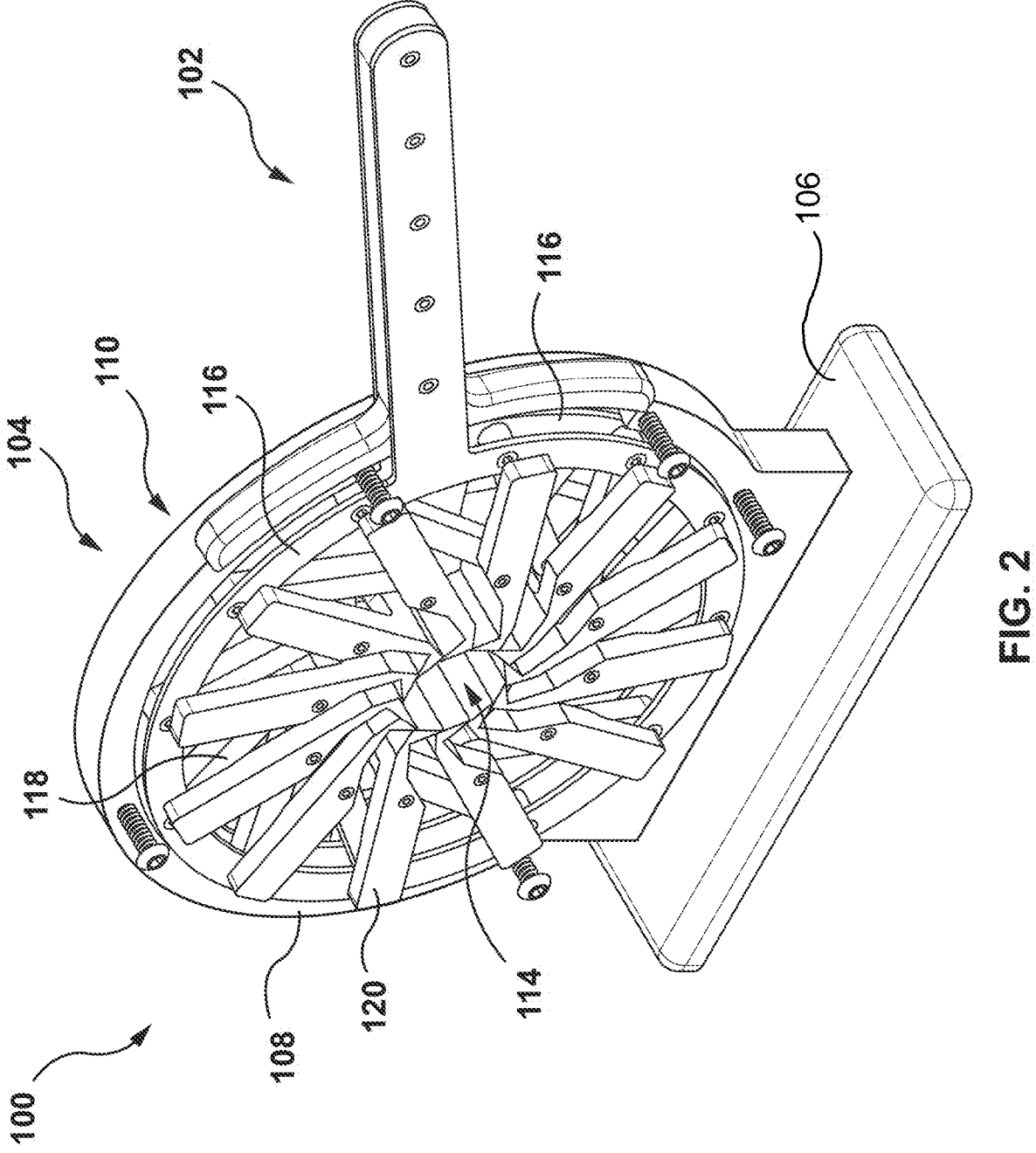
FIG. 2 depicts a perspective view of the crimper of FIG. 1 with a side thereof removed.

FIGS. 1-2 illustrate an example of a crimper 100 in accordance with an embodiment hereof. One skilled in the art will realize that FIGS. 1-2 illustrate one example of a crimper, and that existing components illustrated in FIGS. 1-2 may be removed and/or additional components may be added to the crimper 100. In an embodiment, the crimper 100 may be an iris crimper as described in more detail in U.S. Patent Pub. 2022/0039979A1 to Castelli et al., which is assigned to the same assignee as the present application and herein incorporated by reference in its entirety.

FIG. 1 is a side view of a first side 108 of the crimper 100. The crimper 100 includes a handle 102, a crimper housing 104, and a base 106. The crimper housing 104 includes an opening 112 extending from the first side 108 of the crimper housing 104 to a second side 110. The opening 112 permits access to a crimper chamber 114 of the crimper 100.

FIG. 2 illustrates a perspective view of the crimper 100, in which the second side 110 of the crimper housing 104 has been removed to illustrate internal components of the crimper 100. The handle 102 extends into the crimper housing 104 and includes two cams 116 coupled to a plurality of crimper elements 120 by rods 118. The plurality of crimper elements 120 form the crimper chamber 114. The plurality of crimper elements 120 of the crimper housing 104 function as an iris to decrease or increase the volume of the crimper chamber 114 through the movement of the handle 102. The crimper 100 includes an expanded state wherein the crimper chamber 114 has a first volume V1 when the handle 102 is not actuated, and a compressed wherein the crimper chamber 114 has a second volume V2 when the handle 102 is actuated. The first volume V1 is greater than the second volume V2.

In embodiments herein, the crimper 100 operates to transition a dry valve prosthesis from an uncompressed state to a compressed state. In operation, a dry valve prosthesis may be loaded into the crimper chamber 114. The handle 102 is actuated to transition the dry valve prosthesis from the uncompressed state to the compressed state. A delivery system may be positioned through the dry valve prosthesis in the uncompressed state such that the dry valve prosthesis may be compressed around the delivery system for loading thereon.

To operate the crimper 100, a force may be applied to the handle 102. When the force is applied, the crimper elements 120 move inward generally towards the center of the crimper chamber 114 generating the iris effect. Accordingly, the volume of the crimper chamber 114 decreases from the first volume V1 to the second volume V2, and the crimper elements 120 apply a compressive force to external surfaces of the dry valve prosthesis to transition the dry valve prosthesis the uncompressed state to the compressed state. For example, if the dry valve prosthesis is round or cylindrical in shape, the crimper elements apply a force on the surface of the dry valve prosthesis from various directions as force is applied to the handle 102, thereby compressing the dry valve prosthesis.

The crimper 100 may be utilized with dry valve prostheses that are to be delivered transluminally, e.g., via a catheter, and need to be loaded onto or into a catheter. In this example, the dry valve prosthesis can include a stent or frame, and a dry prosthetic valve attached to the interior of the frame. The stent/frame may be crimped to have a low profile such that the dry valve prosthesis can be delivered through the vessels to a target location in a compressed configuration, and then self-expand or be balloon expanded at the target location, for instance, to replace the native heart valve. For example, a dry valve prosthesis may be typically loaded onto a delivery system or catheter at the time of the implantation procedure, e.g., at a catheter lab by hospital staff.

Turning now to FIGS. 3-6, a dry valve crimping and loading system 200, according to embodiments hereof, is shown. The dry valve crimping and loading system 200 includes a crimper, for example the crimper 100 described above, a dry valve prosthesis 300, and packaging 202. As shown, the dry valve prosthesis 300 generally includes a stent or frame 302 and a prosthetic valve 304 coupled to the frame 302. As described above, the prosthetic valve 304 is a "dry" valve. The frame 302 and prosthetic valve 304 may be similar to frames and prosthetic valves known in the art. The frame 302 may be balloon expandable or may be self-expanding. For example, and not by way of limitation, the frame 302 may be similar to frames described in U.S. Pat. No. 11,648,109 to Medtronic, Inc. or may be similar frames described in U.S. Patent Application Publication No. 2011/0172765 to Nguyen et al., which are incorporated by reference herein in their entirety.

Figure 4:
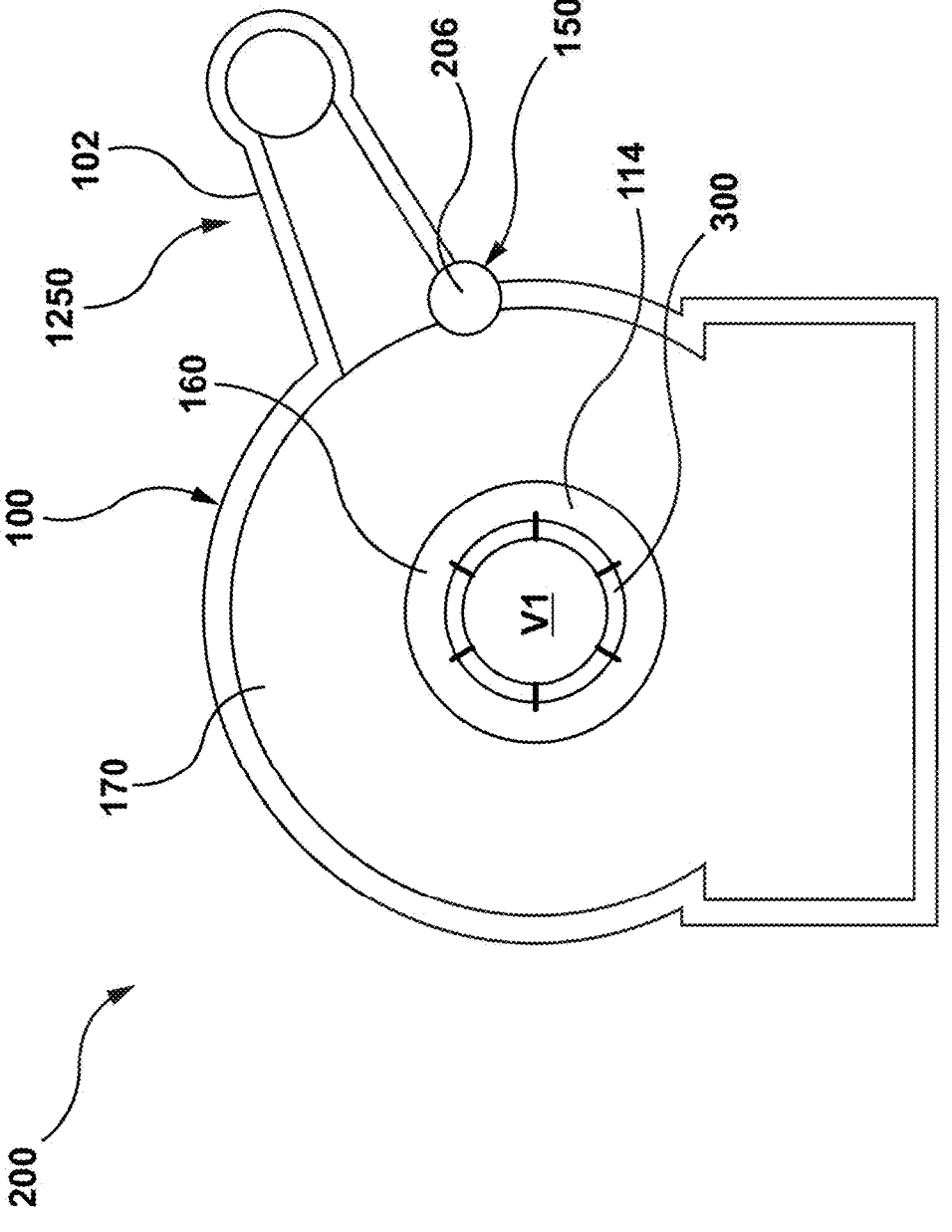
FIG. 4 depicts a side view of the dry valve crimping and loading system of FIG. 3, with the crimper in an expanded state.

In an embodiment dry valve crimping and loading system 200, as shown in FIG. 4, the crimper 100 includes a ratcheting mechanism 150 coupled to the handle 102. In particular, the ratcheting mechanism 150 allows movement of the handle 102 to close the crimper 100 and maintains the handle 102 in the closed position until it is released by a release mechanism. The ratcheting mechanism 150 ensures that the crimper 100 is maintained closed to squeeze out glycerol from the dry prosthetic valve 304. Thus, with such a ratcheting mechanism, the user does not need to hold the handle 102 in the closed position. Further, in an embodiment, the ratcheting mechanism 150 may include a force limiting mechanism configured to limit force on the dry valve prosthesis. Such a force limiting mechanism ensures that excessive force is not applied to the dry valve prosthesis 300, thereby preventing tissue damage, regardless of the size of the dry valve prosthesis 300. A relatively high crimping force may be required to crimp the valve sufficiently to remove the glycerol from the valve. In order to achieve this, a rachet mechanism may be used. Such a mechanism may be comprised of interlocking mechanical teeth to allow movement in only one rotational direction. Such a mechanism may also allow the valve to be maintained under force for a prolonged time without the requirement for a user to hold force, thus allowing further evacuation of glycerol from the valve. For example, and not by way of limitation, a ratchetting ferrule style crimper may be used.

As also shown in FIG. 4, in an embodiment, the crimper 100 may include a force sensor 160. In the embodiment shown, the force sensor 160 is disposed at the crimper chamber 114 to measure the force exerted on the dry valve prosthesis 300. However, this is not meant to be limiting. In other embodiments, the force sensor 160 may be located adjacent to the handle 102 to measure force exerted by the handle 102 as an indication of the force exerted on the dry valve prosthesis 300. In an embodiment, as shown in FIG. 4, the crimper 100 further includes an indicator 170 that notifies a user when the desired force is reached. Thus, the indicator 170 may be operatively linked to the force sensor 160, such as electrically or electronically linked. The indicator 170 may be any type of indicator, such as visual (light, digital display, mechanical movement), auditory, kinesthetic, haptic and/or combinations thereof.

Figure 3:
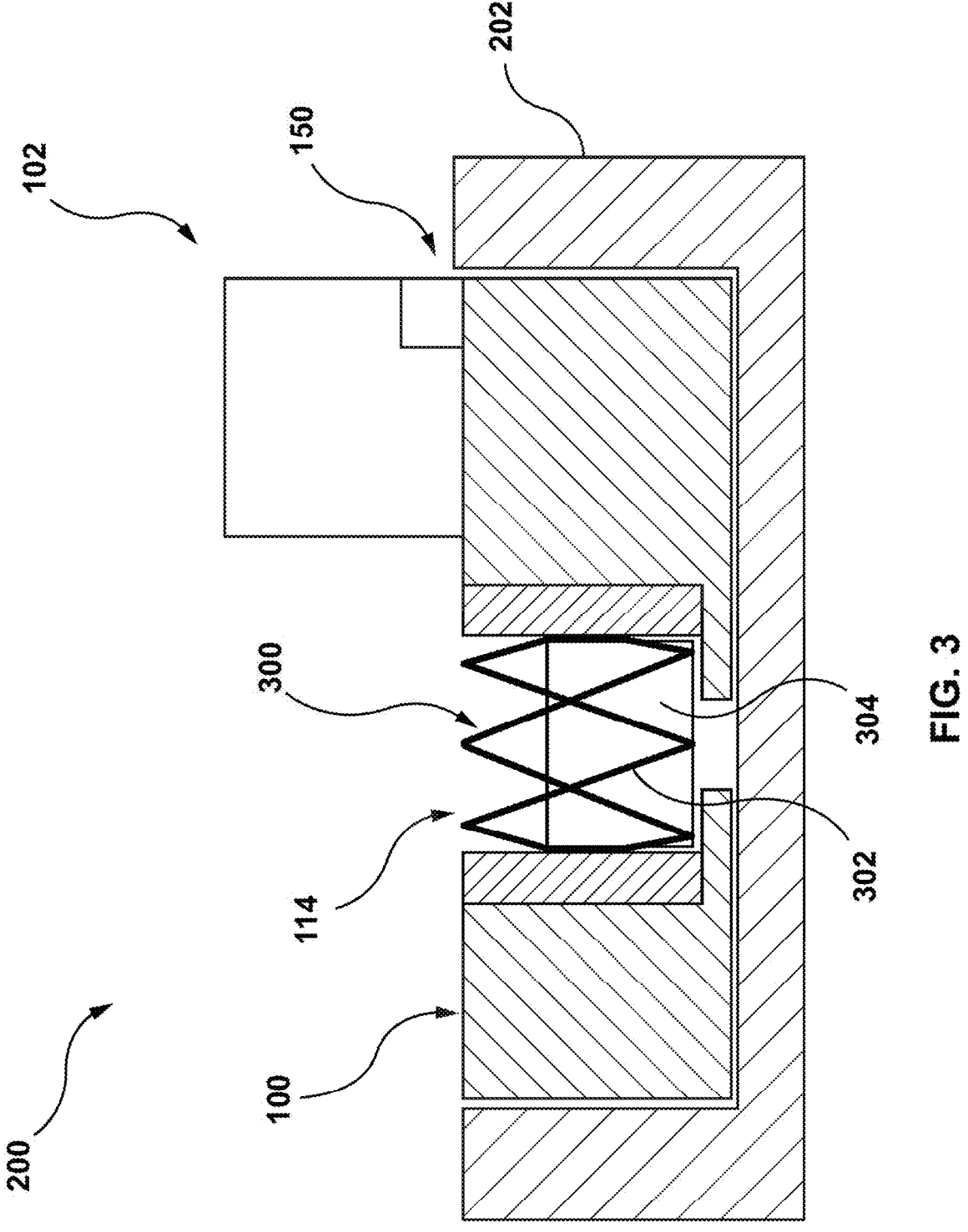
FIG. 3 depicts a schematic cross-sectional view of a dry valve crimping and loading system including a crimper with a dry valve prosthesis disposed therein and disposed in packaging, according to embodiments hereof.

As shown in FIG. 3, any electronics of the dry valve crimping and loading system 200, such as electronics associated with the force sensor 160, may be located above the level of glycerol in the packaging 202, if glycerol is present.

Figure 5:
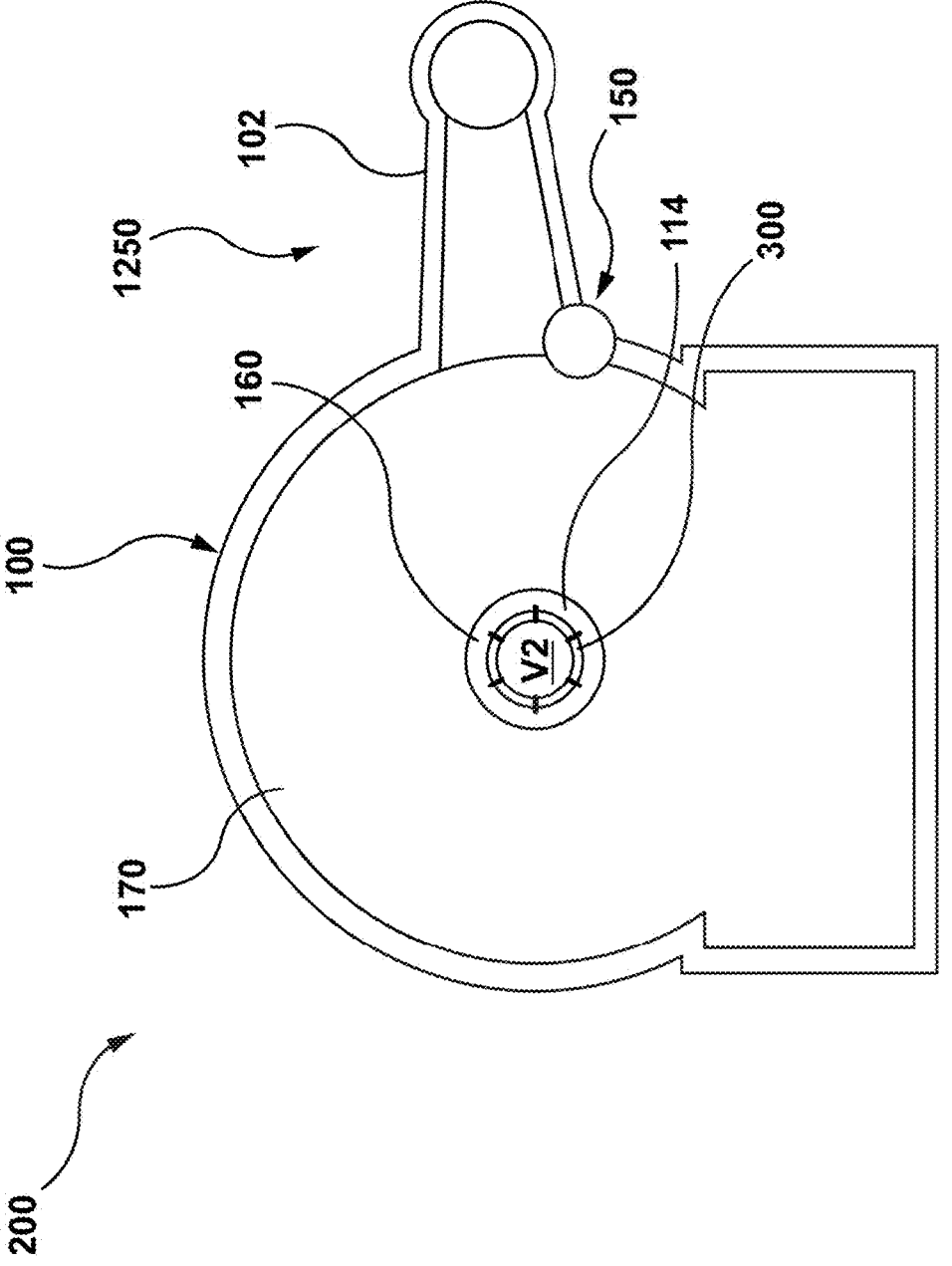
FIG. 5 depicts a cross-sectional view of the dry valve crimping and loading system of FIG. 3, with the crimper in a collapsed state.
Figure 6:
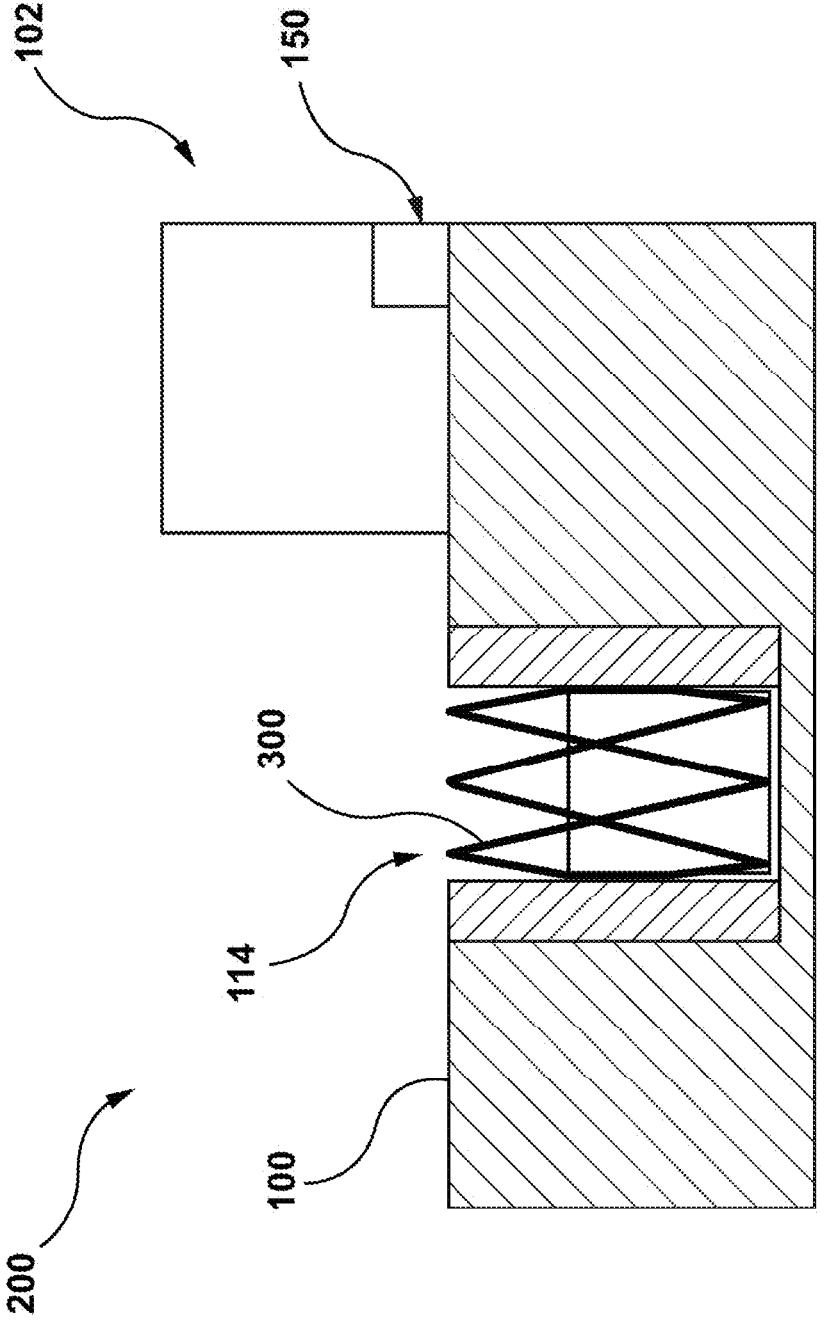
FIG. 6 depicts a side view of the dry valve crimping and loading system of FIG. 3 with the crimper in a collapsed state.

FIGS. 4-6 show the dry valve crimping and loading system 200 in use. FIG. 4 shows the dry valve crimping and loading system 200 in the packaging 202. The crimper 100 in the expanded state. After removing the crimper 100 from the packaging 202, a user may crimp the dry valve prosthesis 300 using the handle 102 of the crimper 100, as shown in FIG. 5. The force limiting mechanism may limit the force applied to the dry valve prosthesis 300. In other embodiments, the force sensor 160 indicates through indicator 170 when the proper amount of crimping force is applied. At such time, the user may release the handle, but the ratcheting mechanism 150 holds the crimper 100 in the crimped position to remove the glycerol from the prosthetic valve 304. Crimping the dry valve prosthesis 300 results in the dry valve prosthesis 300 being in the crimped configuration, as shown in FIG. 6.

Figures 7A, 7B, 7C:
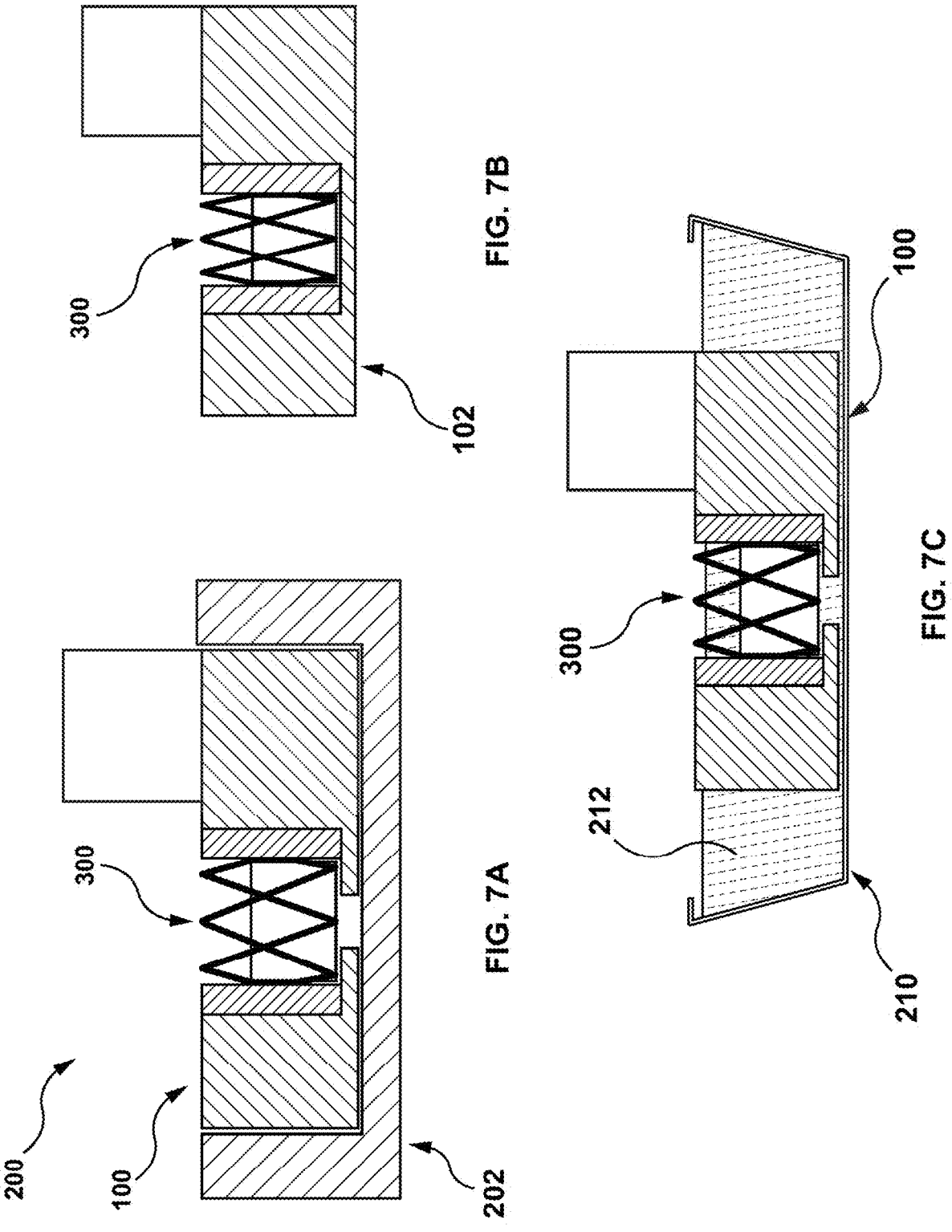
FIGS. 7A-7C depict schematic cross-sectional views of steps of a method of rinsing the dry valve crimping and loading system of FIG. 3 according to embodiments hereof.

In an embodiment, as shown in FIGS. 7A-7C, the crimper 100 including the dry valve prosthesis 300 may be rinsed in a rinse tray 210 prior to crimping. Thus, as shown in FIG. 7A, the crimper 100 including the dry valve prosthesis 300 is in the packaging 202, as described above. As shown in FIG. 7B, the crimper 100 with the dry valve prosthesis 300 disposed therein is removed from the packaging 202. The crimper 100 with the dry valve prosthesis 300 disposed therein may then be placed in the rinse tray 210, which may be filled with a rinse fluid 212, such as saline. The rinse fluid 212 rinses the glycerol from the prosthetic valve 304 of the dry valve prosthesis 300. It will be understood by persons skilled in the art that glycerol expelled from the dry valve prosthesis 300 will readily mix with the saline solution such that remaining traces of the glycerol will rinse out with the saline solution. The rinse tray 700 may be of any configuration suitable for immersing the crimper 100 and the dry valve prosthesis 300 therein. In embodiments wherein the crimper 100 includes electronics such as a force sensor 204, force limiter, or indicators, care should be exercised to prevent damage to the electronics due to exposure or immersion of the electronics in the rinse solution of the rinse tray 700. The crimper 100 may then be removed from the rinse tray 210 and the crimper 100 may be actuated as described above with respect to FIGS. 4-6 to crimp the dry valve prosthesis 300 and squeeze out any remaining glycerol and/or rinsing fluid 212.

Turning now to FIGS. 8-11, a dry valve crimping and loading system 800 according to another embodiment hereof is illustrated. The dry valve crimping and loading system 800 includes a crimper, such as the crimper 100 described above, the dry valve prosthesis 300 as described previously, and packaging 802. In the embodiment of FIGS. 8-11, the packaging 802 forms or includes a rinse tray 810. The crimper 100 and the dry valve prosthesis 300 are disposed within the rinse tray 810.

Figure 8:
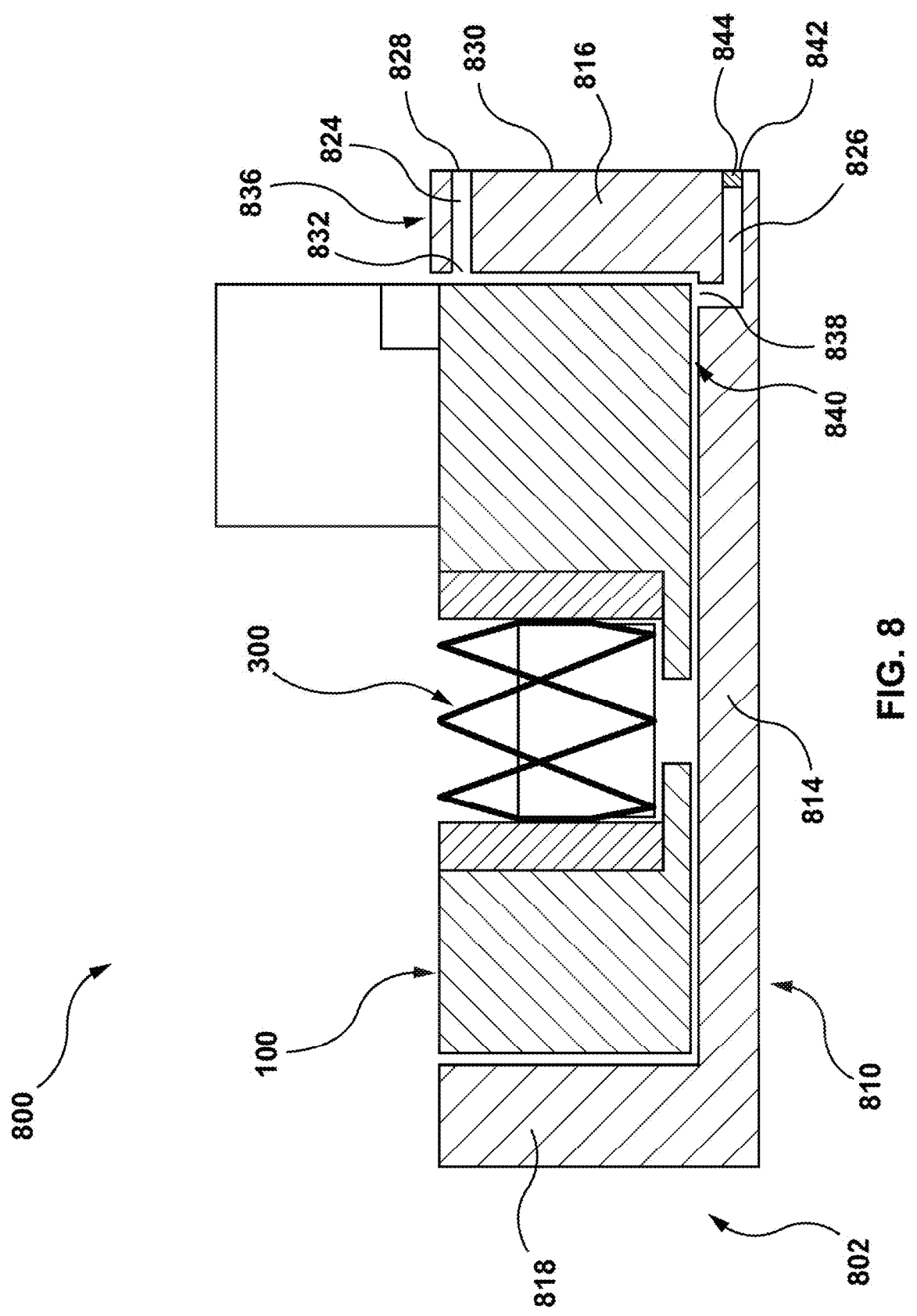
FIG. 8 depicts a cross-sectional view of an embodiment of a dry valve crimping and loading system.
Figure 9:
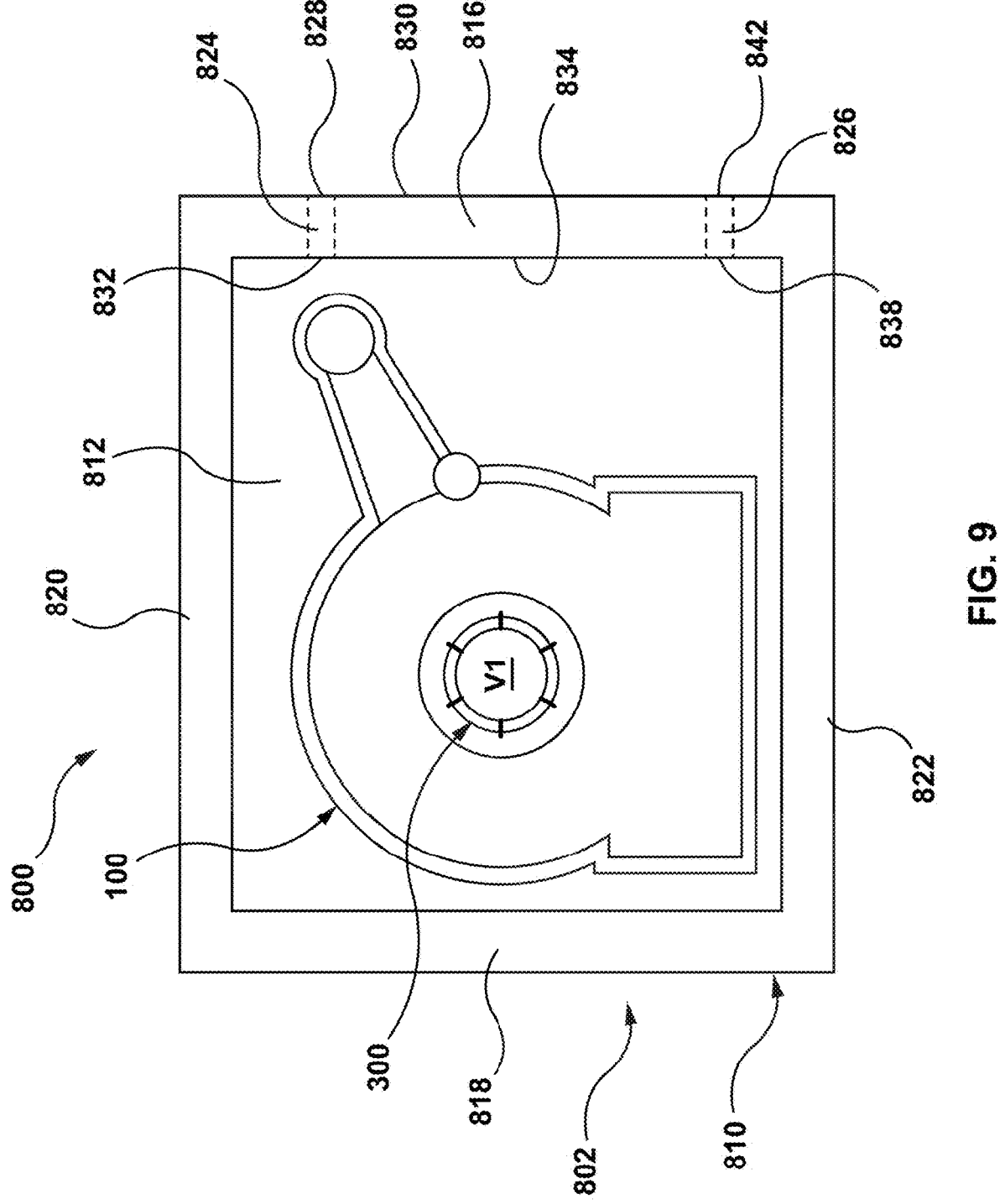
FIG. 9 depicts an overhead view of the dry valve crimping and loading system of FIG. 8.

In an embodiment shown in FIG. 8 and FIG. 9, the rinse tray 810 includes a recess or well 812 defined by a base 814, a first wall 816, a second wall 818, a third wall 820, and a fourth wall 822. The well 812 is configured to receive a portion of the crimper 100 and the dry valve prosthesis 300 therein. In embodiments of FIGS. 8-9, the rinse tray 810 includes an inlet passage 824, an outlet passage 826, and an outlet valve or plug 844. The outlet valve or plug 844 may be a valve, plug, or any other device to selectively allow or prevent out of the outlet passage 826. It will be referred to as an outlet plug 844 as that is shown, but it should be understood that reference to the outlet plug 844 includes valves and other similar devices, as noted. Although not shown, the inlet passage 824 may further include an inlet line and an inlet valve coupled thereto for supplying rinse fluid to the inlet passage 824, as described below. The inlet passage 824 and the outlet passage 826 are in fluid communication with the well 812 and the outside of the rinse tray 810. The inlet passage 824 extends from a fill inlet 828 on an outer surface 830 of the first wall 816 to a fill outlet 832 on an inner surface 834 of the first wall 816. The fill inlet 828 and fill outlet 832 of the inlet passage 824 may be disposed adjacent to an upper edge 836 of the first wall 816. The inlet passage 824 is configured to provide fluid communication to the well 812 such that fluid supplied to the fill inlet 828 will gravity flow into the well 812.

The outlet passage 826 extends from a drain inlet 838 on an inner surface 840 of the base 814 to a drain outlet 842 on the outer surface 830 of the first wall 816. The drain inlet 838 and the drain outlet 842 are disposed adjacent to the base 814 and configured to permit fluid within the well 812 to drain from the well 812 via gravity. The plug 844 may be selectively disposed at the drain outlet 842 of the outlet lumen 826 and is configured to selectively prevent fluid flow from the outlet passage 826 when the plug 844 is disposed at the drain outlet 842, and to permit flow through the outlet lumen 826 when the plug 844 is not disposed at the drain outlet 842. The plug 844 may be formed of any material suitable for the purposes described herein including rubber, cork, or plastic (or it may be a valve or other similar device, as noted above). The plug 844 may be selectively retained within the drain outlet 842 by various methods, non-limiting examples of which include friction, adhesives, or any other method suitable for the purposes described herein. While the plug 844 is depicted in FIG. 8 disposed within the outlet passage 826 at the drain outlet 842, this is not meant to be limiting, and the plug 844 may be disposed at other locations such that fluid flow from the well 812 though the outlet passage 826 is prevented.

While described herein with the inlet passage 824 and the outlet passage 826 extending through the first wall 816, this is not meant to be limiting, and the inlet passage 824 and/or the outlet passage 826 may be in any of the other walls. Further, the inlet passage 824 and the outlet passage 826 need not be disposed in the same wall, as shown in FIG. 8.

With reference to FIGS. 8-11, the use of the dry valve crimping and loading system 800 will now be described. The packaging 802 with the rinse tray 810 incorporated or included therein and the crimper 100 disposed in the rinse tray with the dry valve prosthesis 300 disposed in the crimper 100 may be delivered to a geographic site of a transcatheter heart valve prosthesis procedure (e.g., a hospital).

The rinse tray 810 with the crimper 100 and the dry valve prosthesis 300 disposed therein are removed from any additional packaging of the packaging 202. The rinse tray 810 is delivered with the outlet valve or plug 844 closed/disposed in the drain outlet 842 such that glycerol covering the dry valve prosthesis 300 is prevented from escaping the well 812. The outlet valve or plug 844 is opened/removed such that any glycerol may drain from the well through the outlet passageway 826. As noted above, the dry valve prosthesis 300 is not stored in a liquid. Instead, the leaflets of the dry valve prosthesis 300 may be coated with glycerol. Thus, initial removal of the plug 844 should not result in any glycerol being drained.

Figure 10:
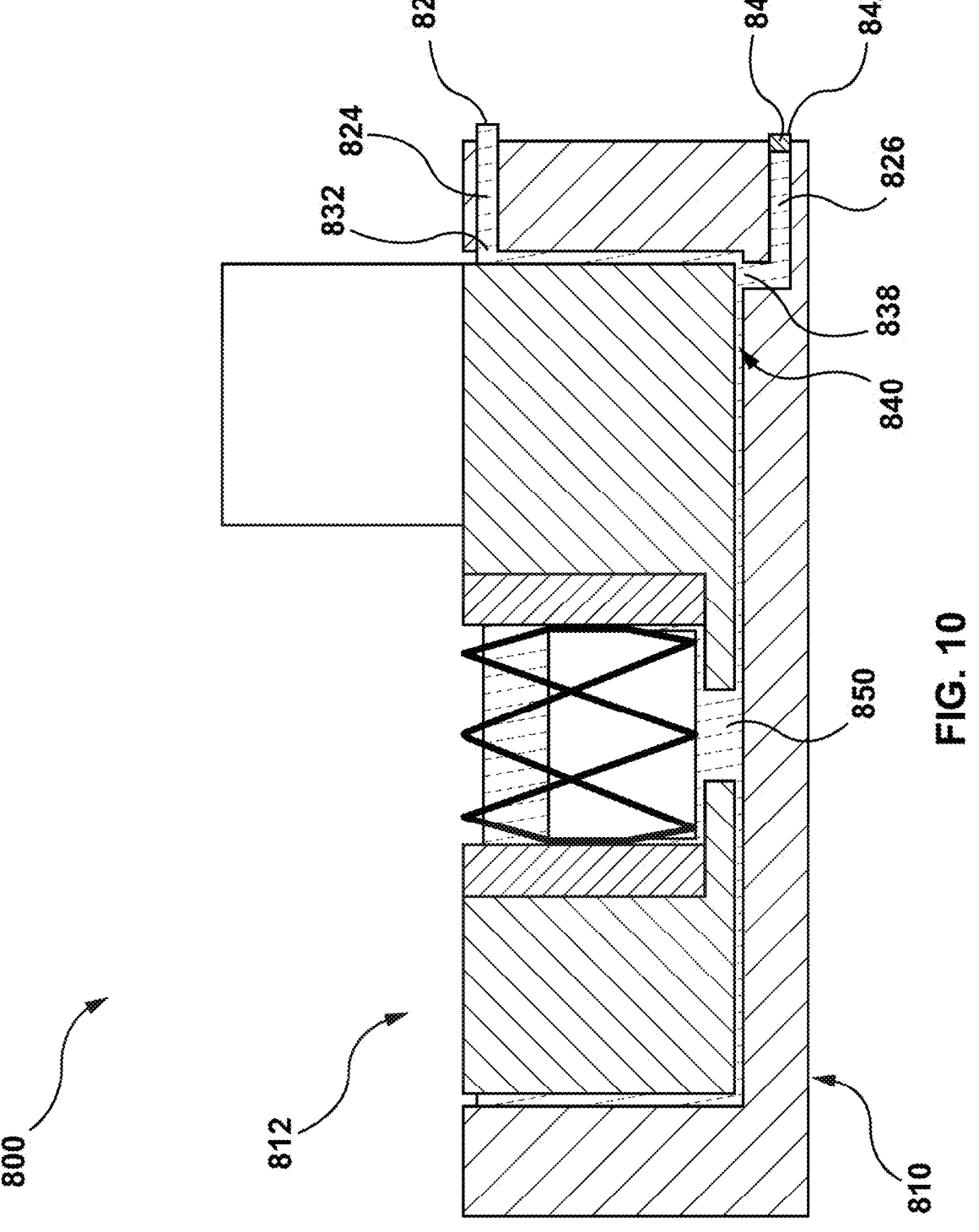
FIG. 10 depicts a cross-sectional view of the dry valve crimping and loading system of FIG. 8.
Figure 11:
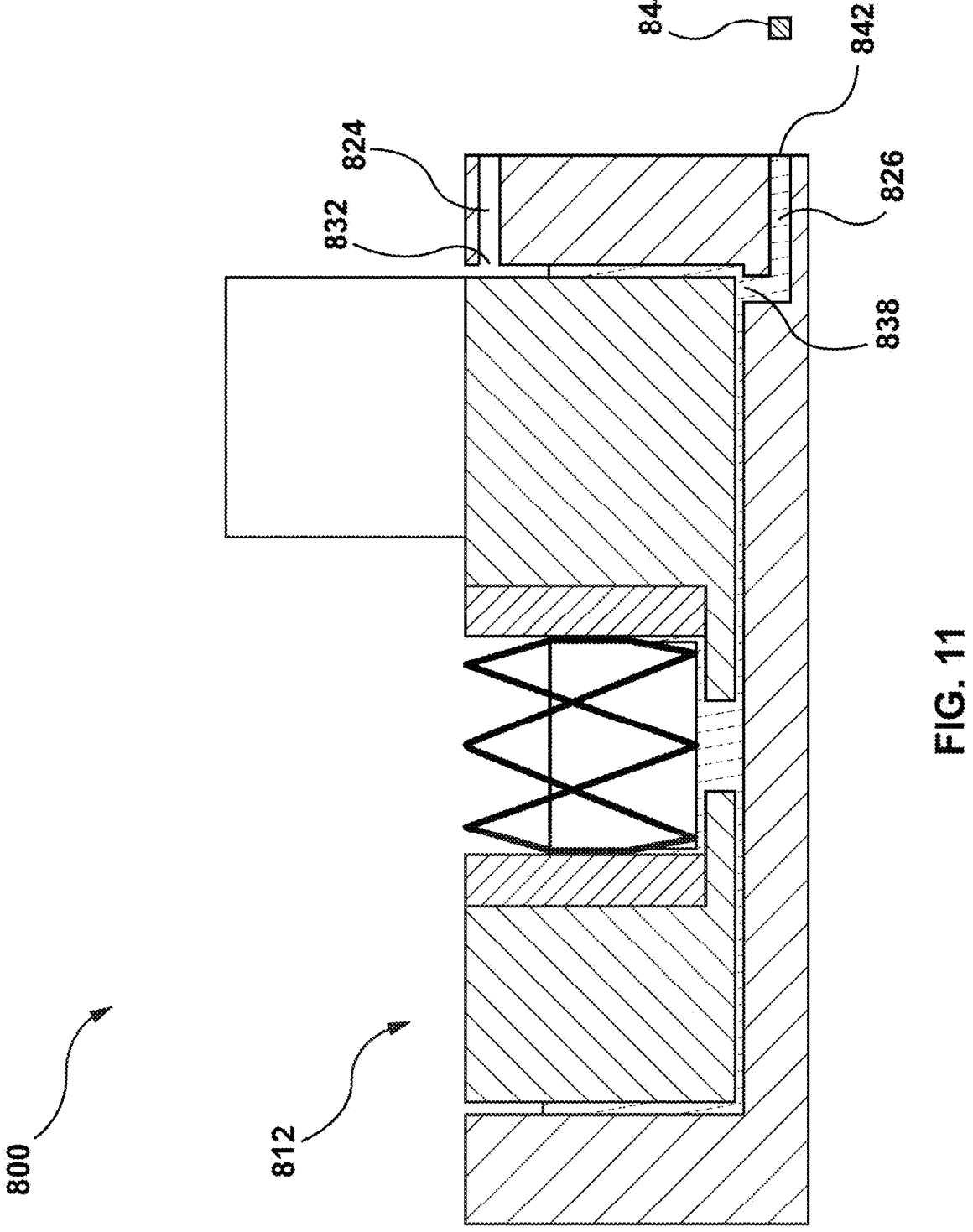
FIG. 11 depicts a cross-sectional view of the dry valve crimping and loading system of FIG. 8.

The outlet valve or plug 844 may then be closed/inserted such that fluid cannot escape the well through the outlet passage 826. The well 812 may then be filled with a rinse fluid 850, such as saline, to cover the dry valve prosthesis 300, as shown in FIG. 10. The outlet valve or plug 844 may then be opened/removed to enable the rinse fluid/remaining glycerol to drain through the outlet passage 826, as shown in FIG. 11. Saline mixes will with glycerol, so use of saline as the rinse fluid should enable the remaining glycerol to drain from the well with the saline. These steps may be repeated at least two more times in keeping with standard rinsing techniques.

Figure 12:
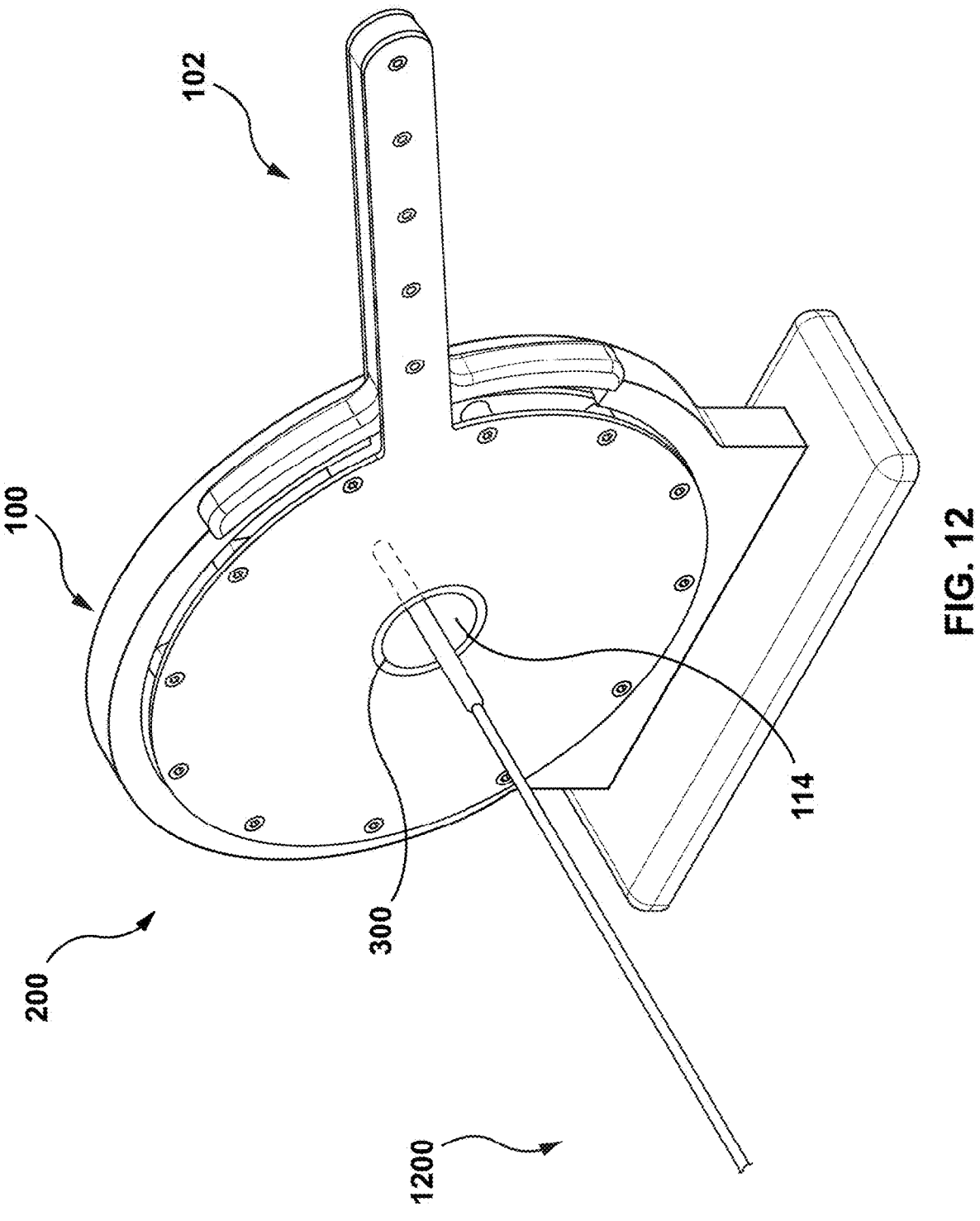
FIG. 12 depicts a delivery system disposed within the dry valve crimping and loading system.

With the glycerol removed from the dry valve prosthesis 300, the crimper 100 with the dry valve prosthesis 300 disposed therein may be removed from the packaging 802/rinse tray 810. The crimper 100 may then be actuated as described above to crimp the dry valve prosthesis 300 onto a delivery system 1200, as shown in FIG. 12.

As noted above, because the dry valve prosthesis 300 does not need to be stored in a fluid, the dry valve prosthesis 300 may be delivered to the geographic site of the procedure (e.g., a hospital) pre-loaded into the crimper 100. By loading the dry valve prosthesis 300 into the crimper 100 at the manufacturing site, machinery/fixturing may be utilized for improved positional accuracy. Further, when at the geographic site of the procedure and the delivery system 1200 is inserted into the crimper chamber 114, positioning features on the crimper 100 and the delivery system 1200 improve the overall positional accuracy of the dry valve prosthesis 300 on the delivery system 1200, thereby also improving accuracy of the final deployment position. Such positioning features may be visual (pad printed marks on the catheter/crimper) or mechanical (stop features in the crimper to position the pre-loaded valve, interlocking features to ensure correct relative positions of crimper, valve and delivery catheter).

Figure 13A:
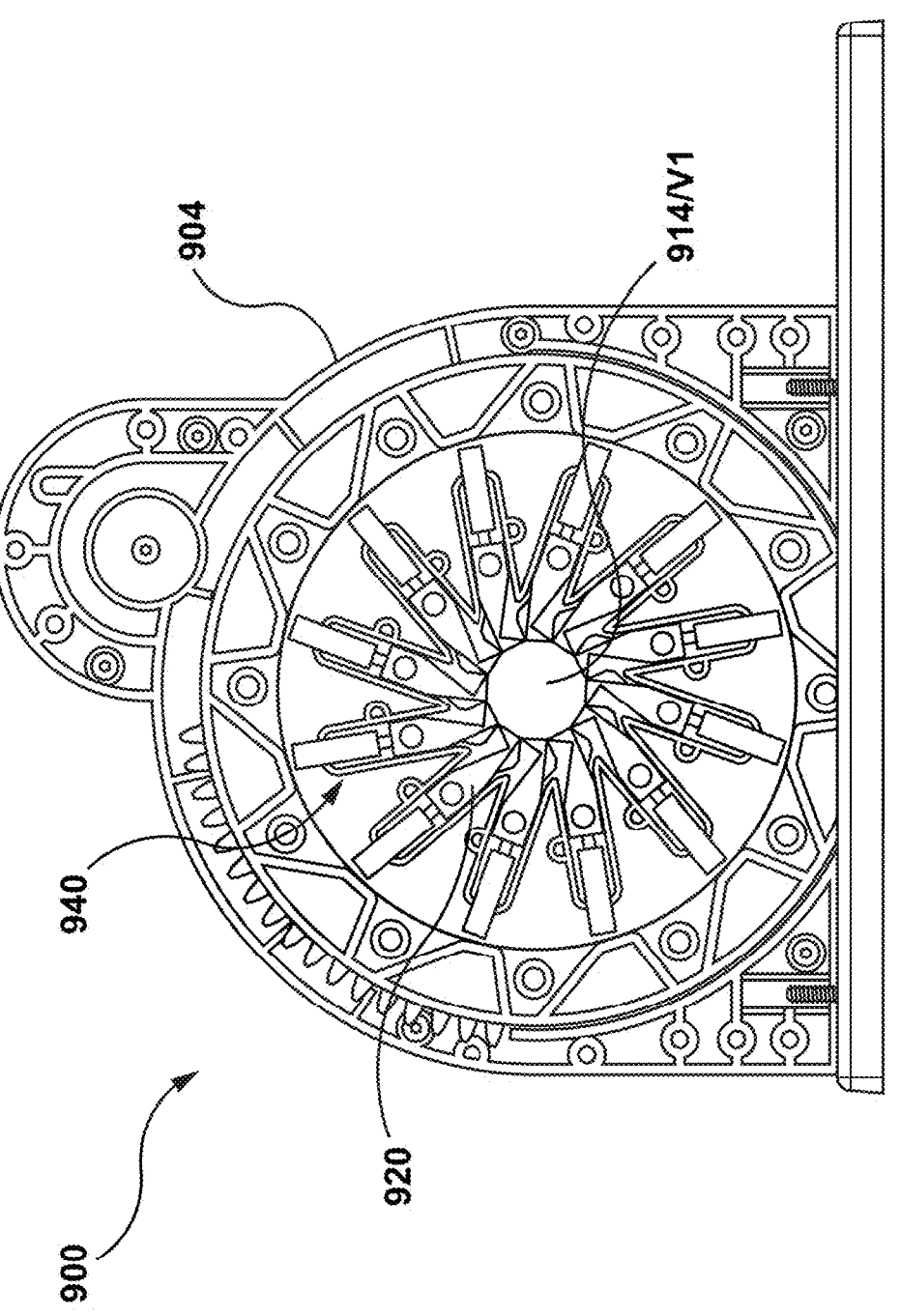
FIGS. 13A-13E depict schematic illustrations of a crimper according to embodiments hereof.
Figure 13B:
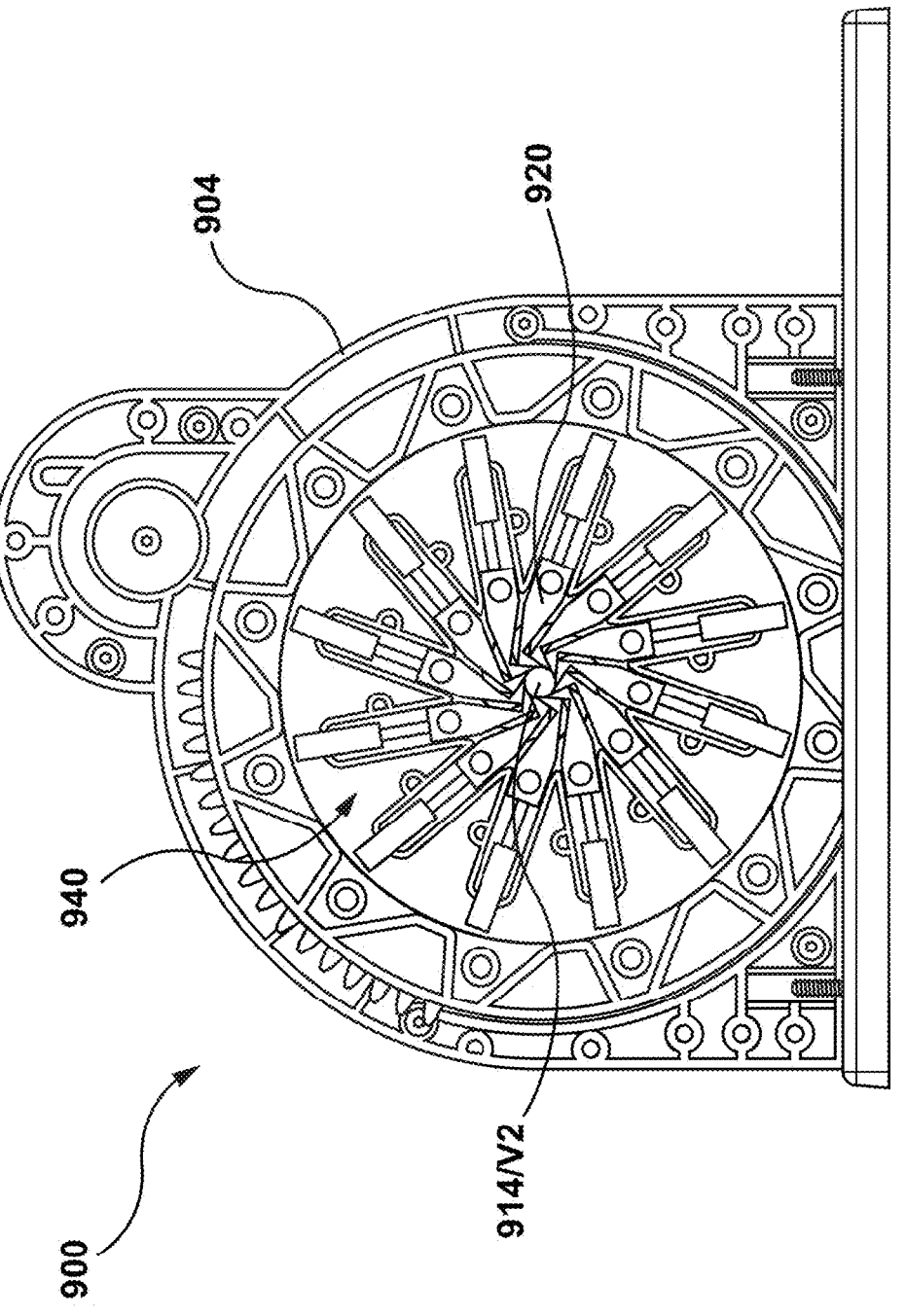
Figures 13C, 13D, 13E:
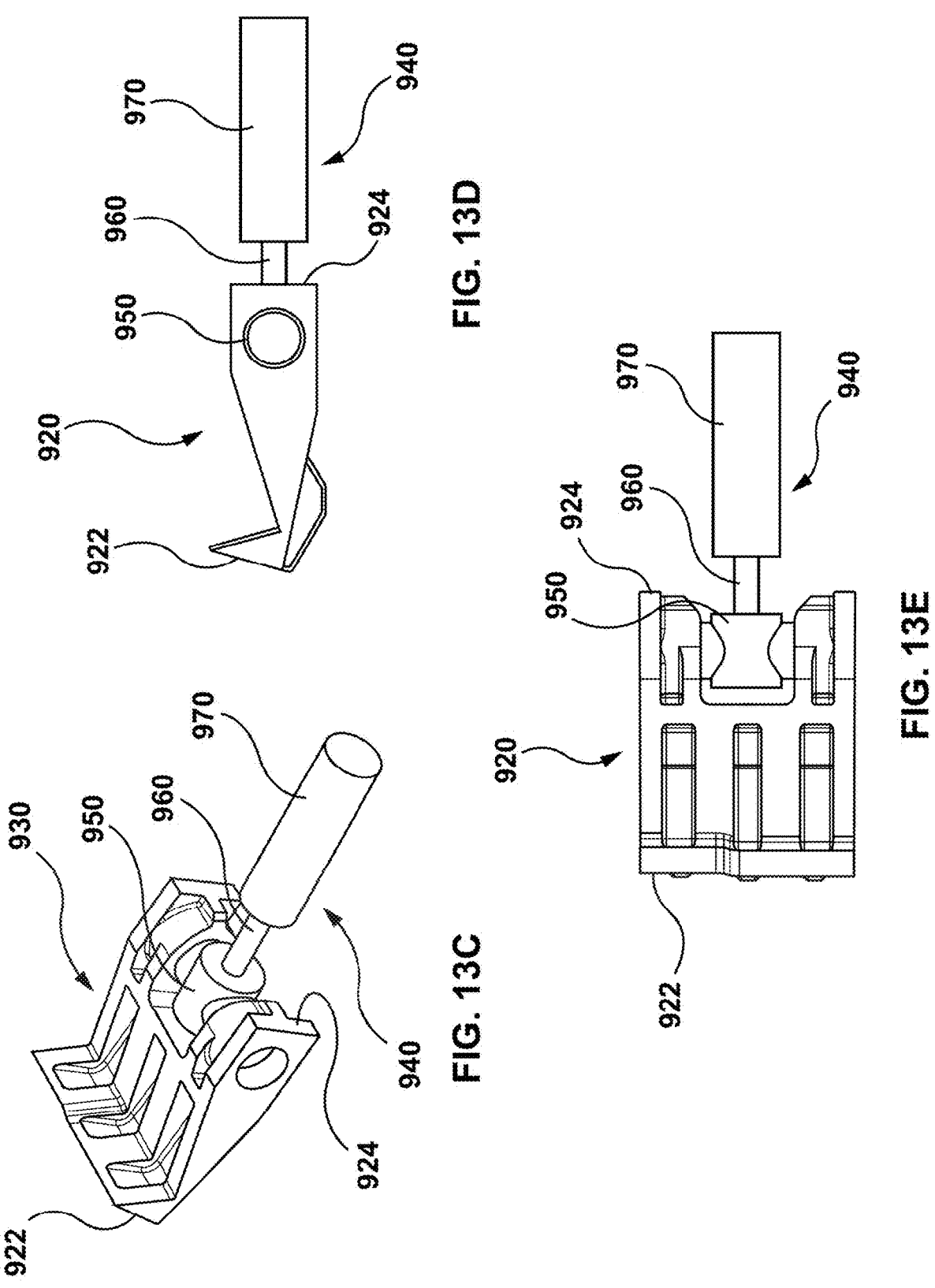

In other embodiments, force imparted on the dry valve prosthesis 300 by a crimper may be controlled by utilizing hydraulic, pneumatic, or electric (solenoid) crimper. In such an embodiment as shown in FIGS. 13A-13E, a crimper 900 includes a crimper housing 904 a plurality of crimper elements 920. The crimper elements 920 function as an iris to decrease or increase the volume of a crimper chamber 914 formed by distal ends 922 of the crimper elements 920. The crimper 900 further includes a plurality of pistons 940. Each piston 940 is coupled to a proximal end 924 of a corresponding crimper element 920. Each piston 940 includes a distal housing 950, a rod 960, and a proximal housing 970. The distal housing 950 is coupled to the proximal end 924 of the corresponding crimper element 920. A distal end of the rod 960 is coupled to the distal housing 950. A proximal end of the rod 950 is disposed within the proximal housing 970 and the rod 960 is slidable within the proximal housing 970. The rods 970 are actuated such that in an unactuated state, as shown in FIG. 13A, the distal ends 922 of the crimper elements 920 are spaced such that the crimper chamber 914 has a first volume V1. In other words, the rods 960 are retracted proximally within the proximal housing 970. When the pistons 940 are actuated, as shown in FIG. 13B, the rods 960 are extended distally from the proximal housings 970 and push the distal housings 950, and hence the crimper elements 920, towards the center of the crimper 900. This movement causes the distal ends 922 of the crimper elements to move closer together such that the crimper chamber 914 has a second volume V2 smaller than the first volume V1.

The pistons 920 may be actuated hydraulically, pneumatically, or electrically. For example, and not by way of limitation, the proximal housing 970 may form a hydraulic chamber. When the hydraulic chamber is filled with hydraulic fluid, the rod 960 is pushed distally, thereby actuating the crimper 900. When fluid is drained from the hydraulic chamber, the rod 960 retracts within the proximal housing 970, such as by a spring or other biasing mechanism. The use of a hydraulic, pneumatic, or electrically driven crimper enables more force to be used if needed and provides improved control of the amount of force being used.

While only some embodiments have been described herein, it should be understood that it has been presented by way of illustration and example only and not limitation. Various changes in form and detail can be made without departing from the spirit and scope of the disclosure aspects, and each feature of embodiments discussed herein and of each reference cited herein, can be used in combination with the features of any other embodiment. All patents and publications discussed herein are incorporated by reference herein in their entirety.

What is claimed is:

1. A method for crimping and loading a dry valve prosthesis onto a delivery system with a dry valve crimping and loading system, wherein the dry valve crimping and loading system includes a rinse tray, a crimper disposed within the rinse tray, and the dry valve prosthesis pre-loaded within a crimper chamber of the crimper, the method comprising:

at least partially filling the rinse tray with a rinse solution;

actuating the crimper to transition the crimper chamber from an expanded state to a collapsed state and to compress the dry valve prosthesis to expel glycerol from the dry valve prosthesis;

releasing or disengaging the crimper to transition the crimper chamber from the collapsed state to the expanded state;

removing the crimper and the dry valve prosthesis from the rinse tray;

disposing a distal end of a delivery system within the dry valve prosthesis;

actuating the crimper to transition the crimper chamber from the expanded state to the collapsed state and to transition the dry valve prosthesis from an uncompressed state to a compressed state onto the distal end of the delivery system;

coupling the dry valve prosthesis to the delivery system;

removing the crimper from the dry valve prosthesis and the delivery system; and sterilizing the delivery system and the dry valve prosthesis.

2. The method of claim 1, wherein the crimper of the dry valve crimping and loading system includes a handle, wherein actuation of the handle transitions the crimper chamber from the expanded state to the collapsed state and the dry valve prosthesis from the uncompressed state to the compressed state.

* * * * *